(12) United States Patent
Takamizawa

(10) Patent No.: US 9,575,303 B2
(45) Date of Patent: Feb. 21, 2017

(54) MICROSCOPE APPARATUS

(71) Applicant: OLYMPUS CORPORATION, Shibuya-ku, Tokyo (JP)

(72) Inventor: Nobuhiro Takamizawa, Hachioji (JP)

(73) Assignee: OLYMPUS CORPORATION, Toyko (JP)

( * ) Notice: Subject to any disclaimer, the term of this patent is extended or adjusted under 35 U.S.C. 154(b) by 0 days.

(21) Appl. No.: 13/901,411

(22) Filed: May 23, 2013

(65) Prior Publication Data

US 2013/0314775 A1    Nov. 28, 2013

(30) Foreign Application Priority Data

May 25, 2012  (JP) .................................. 2012-119637

(51) Int. Cl.
  G02B 21/36    (2006.01)
  G02B 21/06    (2006.01)
  (Continued)

(52) U.S. Cl.
  CPC ............. *G02B 21/06* (2013.01); *G01N 21/648* (2013.01); *G01N 21/6458* (2013.01);
  (Continued)

(58) Field of Classification Search
  CPC ....... G02B 21/16; G02B 21/365; G02B 21/06; G02B 21/008; G02B 21/002; G02B 21/0076; G02B 21/18; G02B 2207/113; G02B 21/0032; G02B 21/082; G02B 21/361; G02B 27/0018; G02B 21/0004; G02B 21/0036; G02B 21/0096; G02B 21/086; G02B 21/125; G02B 21/36; G01N 15/1475; G01N 21/6458; G06F 19/321; G06F 19/3406; G06T 3/4038; G01J 1/32; H01L 27/14
  (Continued)

(56) References Cited

U.S. PATENT DOCUMENTS 6,272,235 B1    8/2001  Bacus et al.
6,522,774 B1    2/2003  Bacus et al.
(Continued)

FOREIGN PATENT DOCUMENTS

EP    2 034 349 A1    3/2009
JP    2003-029153 A   1/2003
(Continued)

OTHER PUBLICATIONS

Extended European Search Report (EESR) dated Sep. 26, 2013 (in English) issued in counterpart European Application No. 13169129.7.

(Continued)

*Primary Examiner* — Bumsuk Won
*Assistant Examiner* — Balram Parbadia
(74) *Attorney, Agent, or Firm* — Holtz, Holtz & Volek PC

(57) ABSTRACT

A microscope apparatus includes: an objective lens; a CCD that constructs an image of a sample S; an illumination intensity change unit for adjusting an intensity of excitation light; a sensitivity adjustment unit for adjusting a detection sensitivity by the CCD; a galvanometer mirror for changing a light focusing position of excitation light at a pupil position of the objective lens; a storage unit that stores, for each observation method, a predetermined intensity, a predetermined detection sensitivity, and the light focusing position; and a control unit that switches the observation method, reads out the intensity, the detection sensitivity, and the light focusing position according to the observation method based on a synchronization signal synchronized with a frame signal for constructing an image, and controls the illumination intensity change unit, the sensitivity adjustment unit, and the galvanometer mirror.

4 Claims, 2 Drawing Sheets

(51) Int. Cl.
  *G01N 21/64* (2006.01)
  *G02B 21/16* (2006.01)
  *G02B 21/18* (2006.01)

(52) U.S. Cl.
  CPC ............ *G02B 21/16* (2013.01); *G02B 21/18* (2013.01); *G02B 21/36* (2013.01); *G02B 21/365* (2013.01)

(58) Field of Classification Search
  USPC ........................................ 359/363, 385, 388
  See application file for complete search history.

(56) References Cited

U.S. PATENT DOCUMENTS

| | | | |
|---|---|---|---|
| 2003/0058530 A1 | 3/2003 | Kawano | |
| 2003/0123717 A1 | 7/2003 | Bacus et al. | |
| 2004/0196549 A1 | 10/2004 | Aono | |
| 2004/0236773 A1 | 11/2004 | Bacus et al. | |
| 2005/0179903 A1 | 8/2005 | Tsuruta et al. | |
| 2005/0207005 A1 | 9/2005 | Kawano | |
| 2005/0224692 A1* | 10/2005 | Tsuchiya | G01N 21/6458 250/201.3 |
| 2005/0254696 A1 | 11/2005 | Bacus et al. | |
| 2005/0270639 A1* | 12/2005 | Miki | 359/381 |
| 2007/0268574 A1* | 11/2007 | Sasaki | 359/385 |
| 2008/0251689 A1* | 10/2008 | Yamashita | G01N 21/6456 250/201.3 |
| 2009/0153878 A1* | 6/2009 | Fujii | G01B 11/24 356/601 |
| 2009/0159814 A1 | 6/2009 | Maiya | |
| 2012/0062722 A1 | 3/2012 | Sase | |

FOREIGN PATENT DOCUMENTS

| | | |
|---|---|---|
| JP | 2003-279860 A | 10/2003 |
| JP | 2009-098229 A | 5/2009 |
| WO | WO 98/39728 A1 | 9/1998 |

OTHER PUBLICATIONS

European Office Action dated Nov. 10, 2015, issued in counterpart European Application No. 13169129.7.
European Office Action dated Aug. 10, 2016, issued in counterpart European Application No. 13169129.7.
"Introduction to Acousto-optic Modulators and Deflectors", Retrieved from Internet on Aug. 3, 2016: URL:http://www.optoscience.com/maker/gooch/pdf/IntroductionAO.pdf, Dec. 31, 2009.
Tokunaga, et al., "Single Molecule Imaging of Fluorophores and Enzymatic Reactions Achieved by Objective-Type Total Internal Reflection Fluorescence Microscopy", Biochemical and Biophysical Research Communications, Academic Press Inc., Orlando, FL, US, vol. 235, pp. 47-53, Jan. 1, 1997.

* cited by examiner

MICROSCOPE APPARATUS

CROSS REFERENCE TO RELATED APPLICATIONS

This application claims benefit of Japanese Patent Application No. 2012-119637, the content of which is incorporated herein by reference.

TECHNICAL FIELD

The present invention relates to a microscope apparatus.

BACKGROUND ART

Heretofore, a microscope apparatus capable of observing a sample while switching its observation between an epifluorescence observation and a TIRF (Total Internal Reflection Fluorescence) observation using evanescent light is known (for example, see Japanese Unexamined Patent Application, Publication No. 2003-279860, Japanese Unexamined Patent Application, Publication No. 2003-29153, and Japanese Unexamined Patent Application, Publication No. 2009-98229. Microscope apparatuses disclosed in JP 2003-279860 and JP 2003-29153 have a configuration in which illumination light is moved in a direction perpendicular to an optical axis of an objective lens by causing the illumination light to be refracted by a parallel plate, thereby enabling switching between the TIRF observation and the epifluorescence observation. The microscope apparatus disclosed in JP 2009-98229 has a configuration in which the position of an outlet end of an optical fiber that emits illumination light is switched and thereby the illumination light is moved in a direction perpendicular to an optical axis of an objective lens at the pupil position of the objective lens, thereby enabling switching between the TIRF observation and the epifluorescence observation.

SUMMARY OF INVENTION

Technical Problem

The microscope apparatuses disclosed in JP 2003-279860, JP 2003-29153, and JP 2009-98229 are capable of switching the observation method between the TIRF observation and the epifluorescence observation. However, in order to obtain an appropriate image in each of the observation methods, it is necessary for a user to adjust the intensity of illumination light or the sensitivity of a detector each time the observation method is switched, which requires time.

The present invention has an object to provide a microscope apparatus capable of easily obtaining a suitable image of a sample for each of TIRF observation and epifluorescence observation, while switching the observation between these methods.

Solution to Problem

The present invention provides a microscope apparatus comprising an objective lens that irradiates a sample with illumination light emitted from a light source and concentrates reflected light which reflects from the sample; an image construction unit that detects the reflected light concentrated by the objective lens and constructs an image of the sample; an intensity adjustment unit capable of adjusting an intensity of the illumination light to the sample through the objective lens; a light focusing position change unit capable of changing a light focusing position in a direction that crosses an optical axis of the illumination light at a pupil position of the objective lens; a storage unit that stores, for each observation method which corresponds to a respective light focusing position of the illumination light concentrated on the pupil position of the objective lens, a predetermined intensity of the illumination light to be adjusted by the intensity adjustment unit and the light focusing position of the illumination light to be targeted by the light focusing position change unit; an observation method switching unit capable of switching the observation method; and a control unit that reads out the predetermined intensity of the illumination light and the light focusing position of the illumination light which are stored in the storage unit according to the observation method to be applied by the observation method switching unit based on a synchronization signal synchronized with a frame signal for constructing the image by the image construction unit, and controls an adjustment of the intensity of the illumination light by the intensity adjustment unit and a change of the light focusing position of the illumination light by the light focusing position change unit.

According to the present invention, the light focusing position change unit allows the illumination light to be focused on the center of the pupil at the pupil position of the objective lens, thereby enabling a so-called epifluorescence observation. On the other hand, the light focusing position of the illumination light is shifted from the center of the pupil at the pupil position of the objective lens so that the illumination light is totally reflected by a glass plate, thereby enabling a so-called TIRF (Total Internal Reflection Fluorescence) observation using evanescent light permeated from the glass plate. These observation methods are switched by the observation method switching unit.

In this case, the control unit reads out the predetermined intensity of the illumination light stored in the storage unit, the predetermined detection sensitivity of the image construction unit, and the light focusing position of the illumination light, according to the observation method to be applied by the observation method switching unit based on a synchronization signal synchronized with a frame signal for constructing an image by the image construction unit, and controls the intensity adjustment unit and the light focusing position change unit. This facilitates obtainment of an appropriate image of the sample for each observation method during time lapse imaging in which both the TIRF observation and the epifluorescence observation are employed. Note that a sensitivity adjustment unit for adjusting a detection sensitivity of the image construction unit may be controlled in such a similar manner that the illumination light intensity adjustment unit is controlled.

In the present invention, the intensity adjustment unit may be an acousto-optical element capable of changing a transmittance of the illumination light, a filter device including a plurality of switchable neutral density filters having mutually different transmittances of the illumination light, or an output change device capable of changing an output of the light source.

This configuration facilitates adjustment of the intensity of the illumination light by use of a generally available device. Examples of the acousto-optical element include an AOTF (Acousto-optical Tunable Filter).

In the present invention, the image construction unit may be a two-dimensional imaging element, and the sensitivity adjustment unit may be configured to change an exposure time and/or a gain of the two-dimensional imaging element.

This configuration facilitates adjustment of the detection sensitivity of the reflected light by use of a generally available apparatus.

Advantageous Effects of Invention

The present invention provides an advantageous effect of easily obtaining an appropriate image of a sample for each of TIRF observation and epifluorescence observation, while switching these observation methods.

DESCRIPTION OF EMBODIMENTS

A microscope apparatus according to an embodiment of the present invention will be described below with reference to the drawings.

Figure 1:
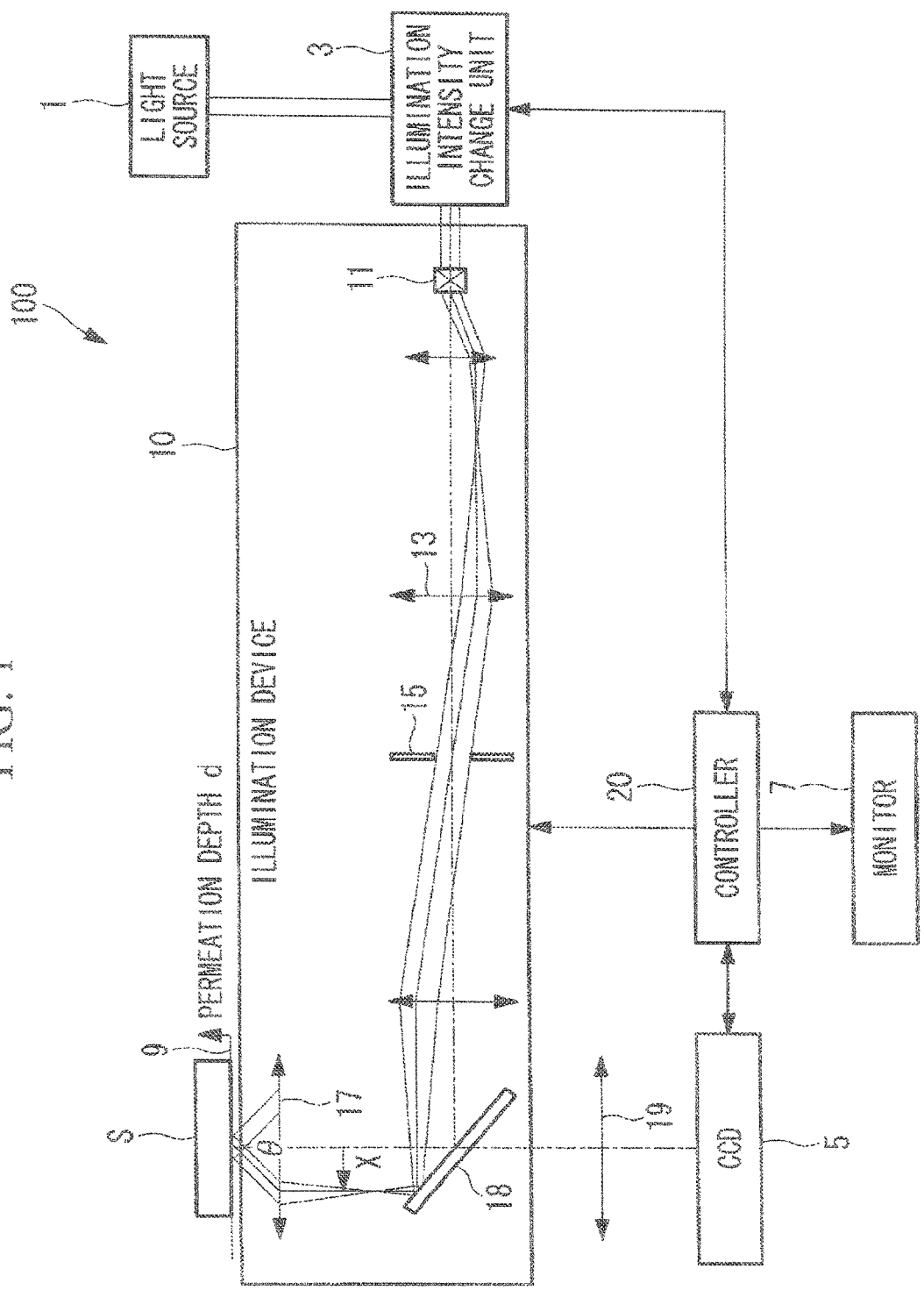
FIG. 1 is a schematic configuration diagram of a microscope apparatus according to an embodiment of the present invention.

As illustrated in FIG. 1, a microscope apparatus 100 according to this embodiment includes the following elements: a light source 1 that emits excitation light (illumination light); an illumination intensity change unit (intensity adjustment unit) 3 capable of adjusting the intensity of excitation light emitted from the light source 1; an illumination device 10 that illuminates a sample S with the excitation light adjusted by the illumination intensity change unit 3; a CCD (Charge Coupled Device: an image construction unit, a two-dimensional imaging element) 5 that detects fluorescence (reflected light) generated from the sample S to construct an image of the sample S; a monitor 7 that displays the image constructed by the CCD 5; and a controller 20, such as a PC (Personal Computer), which controls the illumination intensity change unit 3, the illumination device 10, the monitor 7, and the like.

The sample S is placed on a stage (not illustrated) and is covered by a glass plate 9 such as a slide glass or a cover glass.

As the light source 1, a mercury lamp or a laser light source, for example, is used.

As the illumination intensity change unit 3, a filter wheel (filter device) including a plurality of switchable ND filters (neutral density filters which are not illustrated) having different transmittances of excitation light can be used, for example. This illumination intensity change unit 3 has a configuration in which any one of the ND filters is disposed on a light path for the excitation light by the control of the controller 20. Further, the illumination intensity change unit 3 is configured to change the intensity of the excitation light by switching the ND filter disposed on the light path with another ND filter.

The illumination device 10 includes a galvanometer mirror (light focusing position change unit) 11 capable of deflecting the excitation light whose intensity is adjusted by the illumination intensity change unit 3; a relay lens 13 that relays the excitation light deflected by the galvanometer mirror 11; a field stop (FS) 15 that limits the light flux of the excitation light; an objective lens 17 that irradiates the sample S with the excitation light obtained by limiting the light flux by a field stop 15, and that concentrates the fluorescence from the sample S; and a dichroic mirror 18 that reflects the excitation light made incident on the objective lens 17 from the field stop 15, while allowing the fluorescence, which is concentrated by the objective lens 17 and returns through the light path. Reference numeral 19 denotes an imaging lens that allows the fluorescence transmitted through the dichroic mirror 18 to be formed into an image.

The galvanometer mirror 11 is configured to reflect the excitation light, which is incident from the illumination intensity change unit 3, toward the relay lens 13. This galvanometer mirror 11 is provided so as to oscillate about an optical axis perpendicular to the optical axis of the excitation light, and is controlled by the controller 20 to change an oscillating angle θ. The galvanometer mirror 11 is configured to change the oscillating angle θ to thereby change a light focusing position in a direction that crosses the optical axis of the excitation light at the pupil position of the objective lens 17.

When the galvanometer mirror 11 allows the excitation light to be focused on the center of the pupil at the pupil position of the objective lens 17, the excitation light is made perpendicularly incident substantially along the optical axis of the objective lens 17 with respect to the glass plate 9, so that the excitation light is led to the sample S by so-called epi-illumination.

The fluorescence, which is generated from the sample S and transmitted through the dichroic mirror 18, is photographed by the CCD 5 through the imaging lens 19, thereby enabling the epifluorescence observation. In this case, the fluorescence image of the entire sample S illuminated by epi-illumination can be observed.

On the other hand, when the galvanometer mirror 11 is caused to oscillate to shift the light focusing position of the excitation light in a direction (in FIG. 1, a distance X in the direction perpendicular to the optical axis) perpendicular to the optical axis from the center of the pupil at the pupil position of the objective lens 17, and thereby make the excitation light incident obliquely toward the glass plate 9 so that the excitation light is totally reflected from the glass plate 9, the sample S is illuminated with evanescent light permeated from the glass plate 9.

The fluorescence which is generated from the sample S and transmitted through the dichroic mirror 18 is photographed by the CCD 5 through the imaging lens 19, thereby enabling the TIRF (Total Internal Reflection Fluorescence) observation. In this case, the fluorescence image from the sample S in an area (in FIG. 1, a permeation depth d) in the vicinity of the glass plate 9 illuminated with the evanescent light, that is, in a local area where the evanescent light reaches the sample S, can be observed.

The field stop 15 is configured to adjust the area of irradiation onto the sample S by adjusting the opening size.

The CCD 5 is configured to construct an image of the sample S by photographing the fluorescence image which is transmitted through the dichroic mirror 18 and is formed by the imaging lens 19. The CCD 5 is configured to output, to the controller 20, a frame signal to construct the image.

Figure 2:
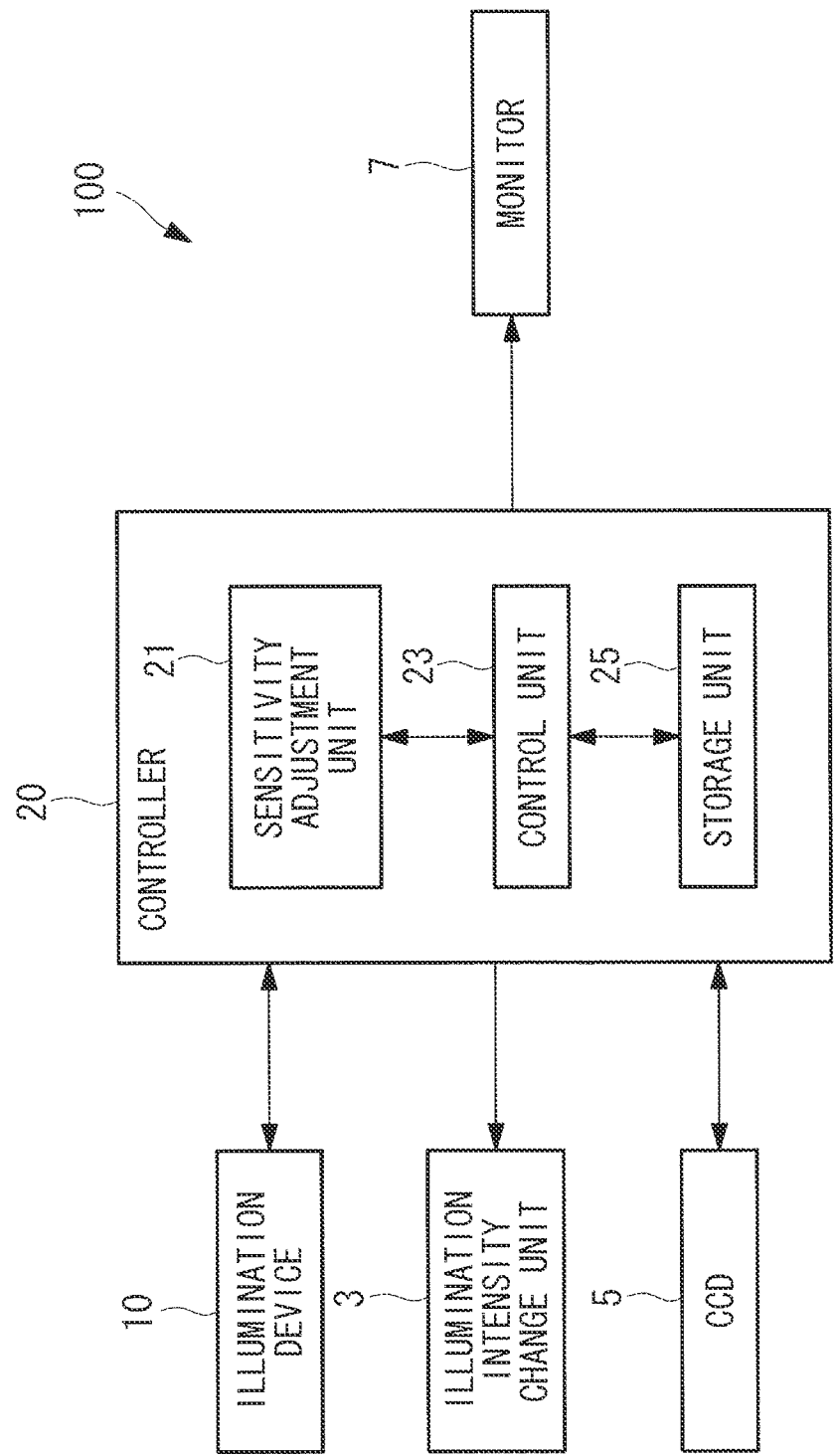
FIG. 2 is a block diagram illustrating a configuration of a controller illustrated in FIG. 1.

As illustrated in FIG. 2, the controller 20 includes the following elements: a sensitivity adjustment unit 21 capable of adjusting the detection sensitivity of the fluorescence by the CCD 5; a control unit 23 that controls the sensitivity adjustment unit 21, the illumination intensity change unit 3, and the illumination device 10; and a storage unit 25. This storage unit 25 stores appropriate control information used by the control unit 23 for carrying out the observation method according to light focusing positions in a direction perpendicular to the optical axis of the excitation light focused at the pupil position of the objective lens 17, that is, appropriate control information used by the control unit 23 in each of the TIRF observation and the epifluorescence observation.

The sensitivity adjustment unit 21 is configured to adjust the detection sensitivity of the fluorescence by the CCD 5 by changing the exposure time and gain of the CCD 5.

As the control information, the storage unit 25 stores, for each of the TIRF observation and the epifluorescence observation, a light focusing position in a direction that crosses the optical axis of the excitation light at the pupil position of the objective lens 17 to be changed by the galvanometer mirror 11, an appropriate intensity of the excitation light adjusted by the illumination intensity change unit 3, and an appropriate detection sensitivity of the CCD 5 adjusted by the sensitivity adjustment unit 21.

The control unit 23 also functions as an observation method switching unit, and is configured to switch the TIRF observation and the epifluorescence observation according to a preset switching pattern. In the epifluorescence observation, the control unit 23 sets the oscillating angle θ of the galvanometer mirror 11 such that the light focusing position in the direction that crosses the optical axis of the excitation light at the pupil position of the objective lens 17 is positioned at the center of the pupil of the objective lens 17. In the TIRF observation, the control unit 23 sets the oscillating angle θ of the galvanometer mirror 11 such that the light focusing position in the direction that crosses the optical axis of the excitation light at the pupil position of the objective lens 17 is located at a position shifted by the distance X in the direction perpendicular to the optical axis from the center of the pupil of the objective lens 17.

The control unit 23 reads out a predetermined intensity of the excitation light, a predetermined detection sensitivity of the CCD 5, and the light focusing position of the excitation light, which are stored in the storage unit 25, according to the observation method switched according to a preset switching pattern based on a synchronization signal synchronized with a frame signal input from the CCD 5. Thus, the control unit 23 controls an adjustment of the intensity of the excitation light by the illumination intensity change unit 3, an adjustment of the detection sensitivity of the CCD 5 by the sensitivity adjustment unit 21, and a change of the light focusing position of the excitation light by the galvanometer mirror 11.

The operation of the microscope apparatus 100 having a configuration as described above will be described.

To observe the sample S while switching the observation between the TIRF observation and the epifluorescence observation by using the microscope apparatus 100 according to this embodiment, the switching pattern for the TIRF observation and epifluorescence observation is input to the control unit 23 beforehand.

Next, the microscope apparatus 100 stores, for each of the TIRF observation and the epifluorescence observation, an appropriate intensity of the excitation light to be adjusted by the illumination intensity change unit 3, an appropriate detection sensitivity of the CCD 5 to be adjusted by the sensitivity adjustment unit 21, and the light focusing position in the direction that crosses the optical axis of the excitation light at the pupil position of the objective lens 17 to be targeted by the galvanometer mirror 11.

When a user instructs the controller 20 to start an observation with an input device (not illustrated), the control unit 23 reads out, from the storage unit 25, the intensity of the excitation light, the detection sensitivity of the CCD 5, and the light focusing position of the excitation light, which are appropriate for the observation, according to the preset switching pattern of the observation method based on the synchronization signal synchronized with the frame signal which is sent from the CCD 5 to construct an image, and the control unit 23 controls each of the illumination intensity change unit 3, the sensitivity adjustment unit 21, and the galvanometer mirror 11.

The excitation light which is emitted from the light source 1 and the intensity of which is adjusted by the illumination intensity change unit 3 is reflected by the galvanometer mirror 11 and relayed by the relay lens 13, and then passes through the field stop 15 and is reflected by the dichroic mirror 18. After that, the excitation light is delivered to the sample S through the glass plate 9 by the objective lens 17. The fluorescence generated from the sample S is concentrated by the objective lens 17 through the glass plate 9 and transmitted through the dichroic mirror 18, and is photographed by the CCD 5 through the imaging lens 19.

In this case, for example, assuming that the first image is set with the TIRF observation in a switching pattern for the observation method, the control unit 23 adjusts the oscillating angle θ of the galvanometer mirror 11, the light focusing position in the direction that crosses the optical axis of the excitation light at the pupil position of the objective lens 17 is shifted by the distance X in the direction perpendicular to the optical axis from the center of the pupil of the objective lens 17. This allows the excitation light to be incident at a totally reflected angle with respect to the glass plate 9. Further, the control unit 23 controls the illumination intensity change unit 3 to adjust the excitation light to have an appropriate intensity for the TIRF observation, and controls the sensitivity adjustment unit 21 to allow the sensitivity adjustment unit 21 to adjust the CCD 5 to have an appropriate detection sensitivity for the TIRF observation.

As a result, the excitation light is totally reflected on the glass plate 9 to thereby locally illuminate the sample S with the evanescent light permeated from the glass plate 9. As the first image, the fluorescence image in an area at a small depth where the evanescent light reaches is obtained by the CCD 5. This enables the TIRF observation of a local area of the sample S.

Subsequently, for example, assuming that the second image is set with the epifluorescence observation in the switching pattern for the observation method, the control unit 23 adjusts the oscillating angle θ of the galvanometer mirror 11, thereby concentrating the excitation light on the center of the pupil at the pupil position of the objective lens 17. This allows the excitation light to be incident perpendicularly to the glass plate 9. Further, the control unit 23 controls the illumination intensity change unit 3 to adjust the excitation light to have an appropriate intensity for the epifluorescence observation, and controls the sensitivity adjustment unit 21 to allow the sensitivity adjustment unit 21 to adjust the CCD 5 to have an appropriate detection sensitivity for the epifluorescence observation.

As a result, the excitation light is illuminated on the sample S along the center of the pupil at the pupil position of the objective lens 17, and the fluorescence image of the entire epi-illuminated sample S is obtained by the CCD 5 as the second image. This allows the epifluorescence observation of the entire sample S.

In this manner, the time lapse imaging in which both the TIRF observation and epifluorescence observation are employed and repeatedly switched according to the predetermined switching pattern is carried out. For each observation method, the control unit 23 changes the intensity of the excitation light, the detection sensitivity of the CCD 5, and the light focusing position of the excitation light, thereby obtaining an appropriate image.

This embodiment illustrates an aspect in which both the intensity of the illumination light and the detection sensitivity of the CCD are adjusted to obtain the appropriate image in each of the TIRF observation and the epifluorescence observation. However, when the appropriate image can be obtained in each of the TIRF observation and the epifluorescence observation only by adjusting the intensity of the illumination light, the adjustment of the detection sensitivity of the CCD 5 may be omitted.

In the microscope apparatus 100 according to this embodiment, the control unit 23 controls the illumination intensity change unit 3 and the galvanometer mirror 11, and the sensitivity adjustment unit 21 as needed, to obtain the predetermined intensity of the appropriate excitation light and the light focusing position of the predetermined excitation light, which are appropriate for the observation method and stored in the storage unit 25, and to obtain the detection sensitivity of the CCD 5 as needed, according to the observation method applied according to the predetermined switching pattern based on the synchronization signal synchronized with the frame signal for forming the image by the CCD 5. This facilitates obtainment of the appropriate image of the sample S for each observation method in the time lapse imaging in which both the TIRF observation and the epifluorescence observation are employed.

The microscope apparatus 100 according to this embodiment can be applied to an observation of a molecular transfer between a cell membrane and a cytoplasm or between a cell membrane and a nucleus, for example. For example, a fluorescently-labeled target molecule is observed in detail by TIRF observation when the target molecule exists in the vicinity of a cell membrane, and is observed by epifluorescence observation when the target molecule exists in a cytoplasm or a nucleus apart from the cell membrane, thereby enabling detailed successive observation of the target molecule.

For example, it is known that when PKC (protein kinase C) is activated by stimulation of phorbol ester or the like, the PKC moves from a cytoplasm to a cell membrane. It is also known that some of receptors existing on the surface of a cell membrane migrates into cytoplasm by ligand binding, and migrate to the surface of the cell membrane again to be reused after disassociation of ligand within the cytoplasm. The microscope apparatus 100 according to this embodiment is capable of observing such a phenomenon in detail.

In this embodiment, a filter device including a plurality of switchable ND filters having different transmittances of excitation light is illustrated as the intensity adjustment unit. For example, in place of the filter device, an acoustooptical element such as an AOTF (Acousto-optical Tunable Filter) may be employed, or an output change device capable of changing an output of the light source 1 may be employed. This configuration facilitates adjustment of the intensity of the illumination light by use of a generally available device.

Further, in this embodiment, the control unit 23 also functions as the observation method switching unit, but the observation method switching unit that switches the observation method according to a preset switching pattern may be provided separately from the control unit 23.

REFERENCE SIGNS LIST

1 LIGHT SOURCE
3 ILLUMINATION INTENSITY CHANGING UNIT (INTENSITY ADJUSTMENT UNIT)
5 CCD (IMAGE CONSTRUCTING UNIT)
11 GALVANOMETER MIRROR (LIGHT FOCUSING POSITION CHANGE UNIT)
17 OBJECTIVE LENS
21 SENSITIVITY ADJUSTMENT UNIT
23 CONTROL UNIT (OBSERVATION METHOD SWITCHING UNIT)
25 STORAGE UNIT
100 MICROSCOPE APPARATUS

The invention claimed is:

1. A microscope apparatus used for TIRF observation, the microscope apparatus comprising:
   an objective lens that irradiates a sample with illumination light emitted from a light source and concentrates reflected light which is reflected from the sample;
   an image construction unit that detects the reflected light concentrated by the objective lens and constructs an image of the sample;
   an intensity adjustment unit that adjusts an intensity of the illumination light to the sample through the objective lens;
   a sensitivity adjustment unit that adjusts a detection sensitivity of the image construction unit for detecting the reflected light;
   a light focusing position change unit that shifts a light focusing position of the illumination light in a direction that is perpendicular to an optical axis of the objective lens at a pupil position of the objective lens, while maintaining a light axis of the illumination light at a position before being irradiated onto the objective lens to be parallel to the optical axis of the objective lens, wherein the illumination light at said position is directed to the objective lens by an optical element without being reflected or refracted by any other optical element between said optical element and the objective lens;
   a storage unit that stores, for each of a plurality of observation methods which corresponds to a respective light focusing position of the illumination light concentrated on the pupil position of the objective lens, a predetermined intensity of the illumination light to be adjusted by the intensity adjustment unit, a predetermined detection sensitivity of the image construction unit to be adjusted by the sensitivity adjustment unit, and the light focusing position of the illumination light to be targeted by the light focusing position change unit;
   an observation method switching unit that switches the observation method in response to a synchronization signal which is synchronized with a frame signal sent from the image construction unit for constructing the image; and
   a control unit that reads out the predetermined intensity of the illumination light, the predetermined detection sensitivity of the image construction unit, and the light focusing position of the illumination light which are stored in the storage unit according to the observation method to be applied by the observation method switching unit based on the synchronization signal, and that controls an adjustment of the intensity of the illumination light by the intensity adjustment unit, an adjustment of the detection sensitivity of the image construction unit by the sensitivity adjustment unit, and a shift of the light focusing position of the illumination light by the light focusing position change unit,
   wherein the light focusing position change unit is configured to shift the light focusing position from a center of the pupil position of the objective lens so as to make the illumination light radiated from the objective lens toward the sample incident obliquely on a glass plate which covers the sample, such that the illumination light is totally reflected by the glass plate and thereby the sample is illuminated with evanescent light permeated from the glass plate for the TIRF observation, and wherein the light focusing position change unit is configured to shift the light focusing position to the center of the pupil position of the objective lens so as to make the illumination light radiated from the objective lens toward the sample incident substantially along the optical axis of the objective lens.

2. The microscope apparatus according to claim 1, wherein the intensity adjustment unit is one of an acousto-optical element capable of changing a transmittance of the illumination light, a filter device including a plurality of switchable neutral density filters having mutually different transmittances of the illumination light, and an output change device capable of changing an output of the light source.

3. The microscope apparatus according to claim 2,
wherein the image construction unit is a two-dimensional imaging element, and
wherein the sensitivity adjustment unit changes at least one of an exposure time and a gain of the two-dimensional imaging element.

4. The microscope apparatus according to claim 1,
wherein the image construction unit is a two-dimensional imaging element, and
wherein the sensitivity adjustment unit changes at least one of an exposure time and a gain of the two-dimensional imaging element.

* * * * *